US009681982B2

(12) United States Patent
Yacono (10) Patent No.: US 9,681,982 B2
(45) Date of Patent: Jun. 20, 2017

(54) WEARABLE USER INTERFACE FOR USE WITH OCULAR SURGICAL CONSOLE

(71) Applicant: Alcon Research, Ltd., Fort Worth, TX (US)

(72) Inventor: Matthew David Yacono, Lake Forest, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 311 days.

(21) Appl. No.: 13/716,680

(22) Filed: Dec. 17, 2012

(65) Prior Publication Data

US 2014/0171959 A1 Jun. 19, 2014

(51) Int. Cl.
| | |
|---|---|
| *A61F 9/007* | (2006.01) |
| *G06F 3/14* | (2006.01) |
| *G02B 21/00* | (2006.01) |
| *G02B 27/01* | (2006.01) |
| *G06F 9/30* | (2006.01) |
| *A61B 90/00* | (2016.01) |

(52) U.S. Cl.
CPC ...... *A61F 9/00745* (2013.01); *G02B 21/0012* (2013.01); *G02B 27/017* (2013.01); *G06F 3/14* (2013.01); *A61B 90/36* (2016.02); *G02B 27/01* (2013.01); *G02B 2027/014* (2013.01); *G06F 9/30* (2013.01); *G09G 2380/08* (2013.01)

(58) Field of Classification Search
CPC ..... A61B 19/201; A61B 19/203; A61B 19/20; A61B 19/52; A61B 1/05; A61B 1/042; A61B 1/04; A61F 9/0008; A61F 9/0017; A61F 9/00781; A61F 9/00736; A61F 9/00745; G06F 3/04815; G06F 8/38
See application file for complete search history.

(56) References Cited

U.S. PATENT DOCUMENTS

| | | | |
|---|---|---|---|
| 4,202,037 A | 5/1980 | Glaser et al. | |
| 4,544,243 A | 10/1985 | Munnerlyn | |
| 5,303,085 A | 4/1994 | Rallison | |
| 5,450,143 A | 9/1995 | Rowe et al. | |
| 5,619,377 A | 4/1997 | Rallison | |
| 5,642,227 A | 6/1997 | Rallison | |

(Continued)

FOREIGN PATENT DOCUMENTS

| | | |
|---|---|---|
| JP | 2001-142003 | 5/2001 |
| JP | 2009-153785 | 7/2009 |

(Continued)

OTHER PUBLICATIONS

International Search Report and Written Opinion issued for PCT/US2013/074117 dated Feb. 14, 2014, 10 pgs.

(Continued)

*Primary Examiner* — Jocelin Tanner (57) ABSTRACT

An ocular surgical system includes a surgical console having a fluidics subsystem, an input pedal subsystem, and a phacoemulsification subsystem. It also includes a wearable user interface in communication with the console. The wearable user interface comprising an interface display having a centrally disposed surgical viewing area and having a peripheral data display region configured to display data relating to the surgery or the console. The peripheral data display region may display information received from the surgical console.

12 Claims, 7 Drawing Sheets

(56) References Cited

U.S. PATENT DOCUMENTS

| | | |
|---|---|---|
| 5,673,151 A | 9/1997 | Rallison |
| 5,880,773 A | 3/1999 | Suzuki |
| 5,969,791 A | 10/1999 | Rowe |
| 5,991,087 A | 11/1999 | Rallison |
| 6,251,113 B1 | 6/2001 | Appelbaum et al. |
| 6,847,336 B1 | 1/2005 | Lemelson et al. |
| 7,460,305 B2 | 12/2008 | Powell et al. |
| 7,519,223 B2 | 4/2009 | Dehlin et al. |
| 7,763,015 B2 | 7/2010 | Cooper et al. |
| 7,777,960 B2 | 8/2010 | Freeman |
| 7,784,946 B2 | 8/2010 | LeBlanc |
| 7,800,820 B2 | 9/2010 | Awdeh |
| 7,855,743 B2 | 12/2010 | Sako et al. |
| 7,901,072 B1 | 3/2011 | Eagan et al. |
| 7,981,109 B2 | 7/2011 | Avanzino et al. |
| 7,983,771 B2 | 7/2011 | Boukhny et al. |
| 8,066,375 B2 | 11/2011 | Skogo et al. |
| 8,631,802 B2 | 1/2014 | Essex et al. |
| 2005/0203380 A1 | 9/2005 | Sauer et al. |
| 2005/0277913 A1* | 12/2005 | McCary ............ 606/1 |
| 2006/0114175 A1 | 6/2006 | Boukhny |
| 2006/0142657 A1* | 6/2006 | Quaid et al. ........... 600/424 |
| 2006/0247659 A1 | 11/2006 | Moeller et al. |
| 2007/0008624 A1 | 1/2007 | Hirayama |
| 2007/0081078 A1 | 4/2007 | Cummings et al. |
| 2007/0164990 A1 | 7/2007 | Bjorklund et al. |
| 2007/0167702 A1 | 7/2007 | Hasser et al. |
| 2007/0202479 A1 | 8/2007 | Todd et al. |
| 2008/0123183 A1* | 5/2008 | Awdeh ............ 359/368 |
| 2008/0216171 A1 | 9/2008 | Sano et al. |
| 2008/0243142 A1 | 10/2008 | Gildenberg |
| 2009/0036902 A1 | 2/2009 | DiMaio et al. |
| 2009/0048587 A1* | 2/2009 | Avanzino et al. ............ 606/10 |
| 2009/0049397 A1 | 2/2009 | Boukhny |
| 2009/0125849 A1 | 5/2009 | Bouvin et al. |
| 2009/0231485 A1 | 9/2009 | Steinke |
| 2009/0270678 A1 | 10/2009 | Scott et al. |
| 2010/0217278 A1* | 8/2010 | Tripathi .................. 606/130 |
| 2010/0277411 A1 | 11/2010 | Yee et al. |
| 2010/0281438 A1 | 11/2010 | Latta et al. |
| 2011/0093821 A1 | 4/2011 | Wigdor et al. |
| 2011/0279666 A1 | 11/2011 | Strombom et al. |
| 2012/0105483 A1* | 5/2012 | Fedorovskaya ...... G02B 27/017 345/660 |
| 2012/0330129 A1* | 12/2012 | Awdeh .................. 600/411 |
| 2013/0021374 A1* | 1/2013 | Miao et al. .............. 345/633 |
| 2013/0041368 A1* | 2/2013 | Cunningham et al. ......... 606/34 |

FOREIGN PATENT DOCUMENTS

| | | |
|---|---|---|
| JP | 2010-536423 | 12/2010 |
| WO | WO 2009023408 A1 | 2/2009 |
| WO | WO 2010/067267 | 6/2010 |
| WO | WO 2011/053921 A2 | 5/2011 |
| WO | WO 2012/137067 | 10/2012 |

OTHER PUBLICATIONS

Lumus, Professional Market Products, Lumus LTD, Jul. 12, 2016, 2 pages. http://lumus-optical.com/?option=com_content&task=view&id=1.

Vuzix, Augmented Reality, Start 1200, Jul. 13, 2016, pp. 1-2. https://www.vuzix.com/Products/LegacyProduct/6.

European Patent Office, Supplementary European Search Report for corresponding Application No. 13864678.1 dated May 31, 2016, 8 pages.

Japanese Patent Office, Office Action for corresponding Application No. 2015-547468 dated May 20, 2016, 3 pages.

* cited by examiner

WEARABLE USER INTERFACE FOR USE WITH OCULAR SURGICAL CONSOLE

BACKGROUND

The devices, systems, and methods disclosed herein relate generally to surgical systems and methods for using a wearable user interface.

Because of the fine and sensitive nature of ocular surgeries, surgeons use magnification devices, such as microscopes, for visualization and magnification of a surgical site. However, surgery under a microscope poses several challenges because the surgical site can be viewed only when the eyes are directly aligned with the oculars. Therefore, when a surgeon desires to check settings or surgical parameters of the surgical system, he or she must pause the surgery, change his or her gaze from the surgical site to a surgical console that may show the settings, and then turn back to the surgical site. While this may take only a few seconds each time, the multiple pauses decrease the efficiency of the surgery, and may result in fewer surgeries that can be scheduled for a single day.

In addition, during the procedure, the surgeon often must hold his head at an awkward angle in order to look through the microscope. Over time, fatigue may make this position uncomfortable.

The present disclosure is directed to devices, systems, and methods that address one or more of the disadvantages of the prior art.

SUMMARY

In an exemplary aspect, the present disclosure is directed to an ocular surgical system, including a surgical console having a fluidics subsystem, an input pedal subsystem, and a phacoemulsification subsystem. It also includes a wearable user interface in communication with the console. The wearable user interface comprising an interface display having a centrally disposed surgical viewing area and having a peripheral data display region configured to display data relating to the surgery or the console. The peripheral data display region may display information received from the surgical console.

In one aspect, a camera is in communication with the wearable user interface, the user interface being arranged to display images captured by the camera in the centrally disposed surgical viewing area. In one aspect, the system includes a microscope for viewing a surgical site, the wearable user interface being configured to permit a user to look through the microscope and simultaneously view the peripheral data display region. In one aspect, the user interface comprises a peripheral viewing region that permits viewing through the wearable user interface.

In an exemplary aspect, the present disclosure is directed to an ocular surgical system, including a surgical console having a fluidics subsystem, an input pedal subsystem, a phacoemulsification subsystem, and a camera configured to communicate live video of an ocular surgical site. It also includes a wearable user interface in communication with the console and configured to receive the live video of the surgical site communicated from the camera. The wearable user interface may include an interface display having a centrally disposed surgical viewing area that displays the live video of the ocular surgical site and having a peripheral data display region configured to display data relating to the surgery or the console. The peripheral data display region may display information received from the surgical console.

In one aspect, a second camera is disposed on the wearable user interface. The second camera may be configured to communicate live video, and the wearable user interface may be configured to simultaneously display the live video from the second camera and the live video of the surgical site.

In another exemplary aspect, the present disclosure is directed to a method including detecting intraocular pressure of a patient undergoing ocular surgery, receiving at a wearable user interface system a signal representing information relating to the detected intraocular pressure, and displaying the information relating to intraocular pressure on a peripheral portion of a display screen on the wearable user interface system.

In one aspect, the method includes receiving at the wearable user interface system a signal representing irrigation and aspiration settings for performing the ocular surgery, and displaying the information relating to intraocular pressure on the peripheral portion of a display screen on the wearable user interface system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein display information on a wearable user interface that shows the status of an ocular surgical system to a surgeon performing the ocular surgery, while also permitting the surgeon to see the surgical site. In one example, it does this with an informational peripheral data display region or frame about a central surgical viewing area that may be used to view the surgical site. As such, the surgeon may continue to perform the surgery while visually being made aware of changing states or measured parameters during the surgery. This may increase the efficiency of the surgery, benefiting both the surgeon and the patient.

In addition, the devices, systems, and methods described herein provide a surgeon with a more comfortable surgical setting by permitting a surgeon to view a surgical site for an ocular surgery outside of a microscope. In some aspects, the surgeon observes the surgical site through a wearable user interface carried on and moveable with a surgeon's head so that the surgeon can view the surgical site without bending over the microscope. In addition, information regarding the surgical system may also be presented to the surgeon so that the surgeon can be aware of the status of the surgical equipment and the eye.

Figure 1:
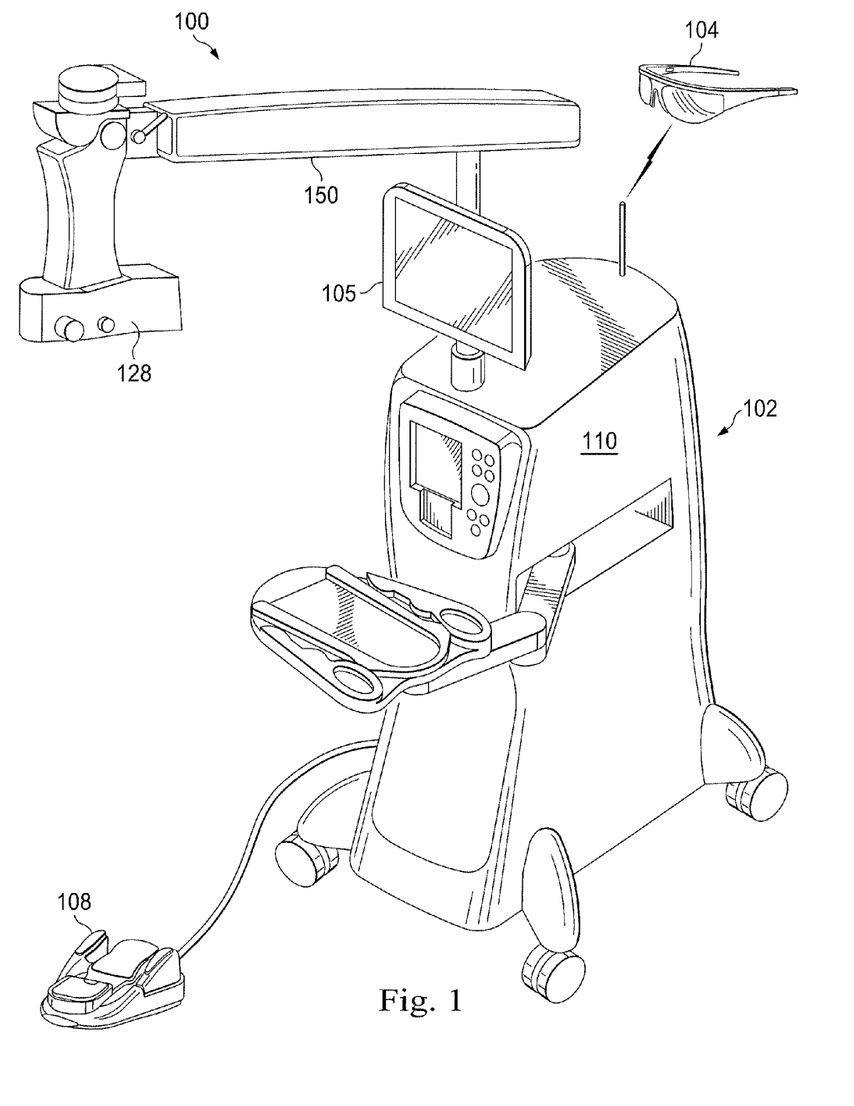
FIG. 1 illustrates a perspective view of an exemplary surgical system according to an embodiment consistent with the principles of the present disclosure.

FIG. 1 shows an exemplary surgical system 100 for treating an ophthalmic condition. In the embodiment shown the surgical system includes a console 102 for performing a surgery and includes a wearable user interface 104.

Figure 2:
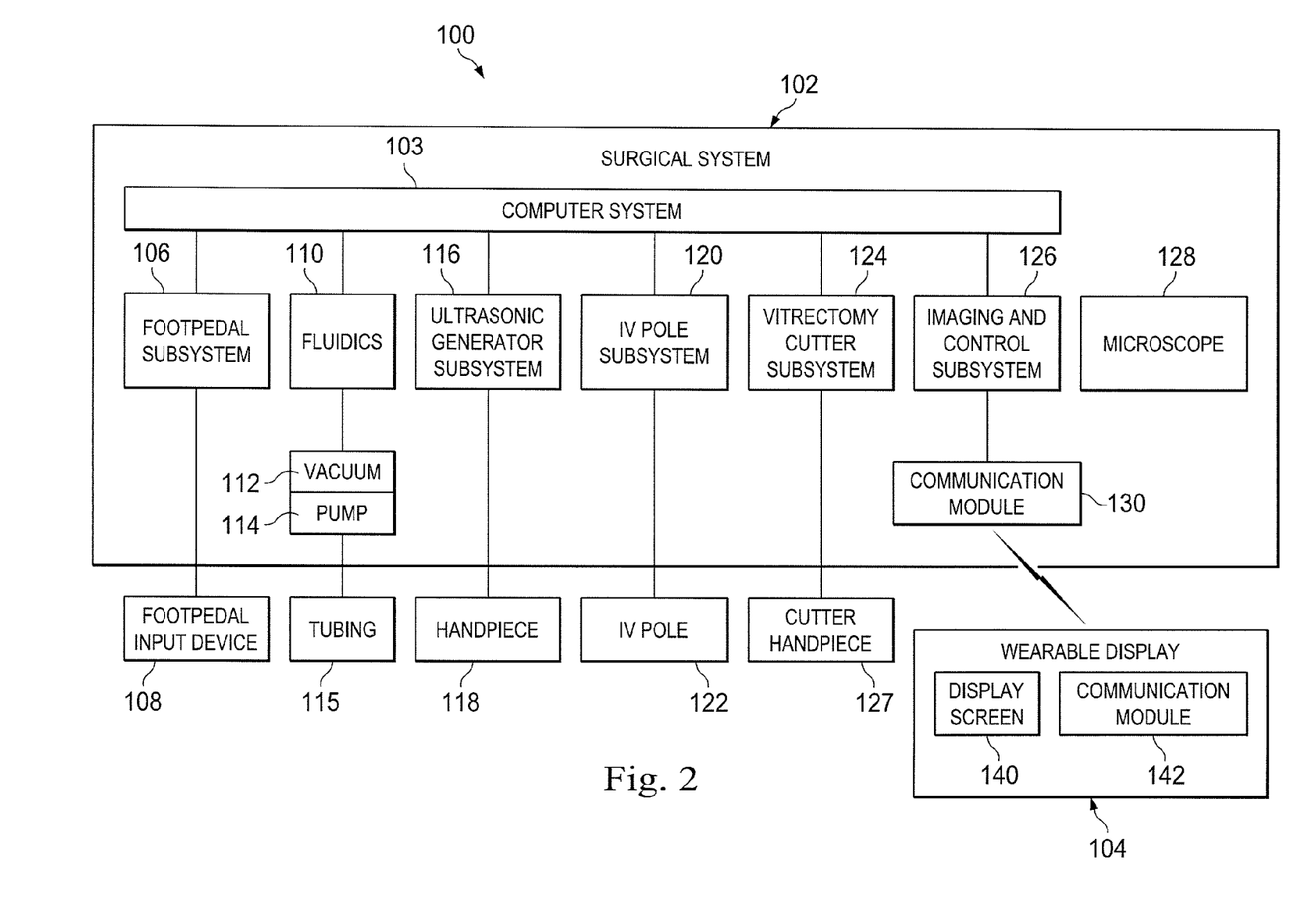
FIG. 2 is an illustration of an exemplary block diagram of the surgical system of FIG. 1 according to an aspect consistent with the principles of the present disclosure.

The console 102 is a surgical console configured and arranged to perform a surgical procedure, such an ocular surgical procedure on a patient. In one embodiment, the surgical console is a phacoemulsification surgical console. FIG. 2 is a block diagram of the system 100 including the console 102 and the wearable user interface 104.

The console 102 includes a computer unit 103, a display screen 105, and a number of subsystems that are used together to perform ocular surgical procedures, such as emulsification or vitrectomy surgical procedures, for example. For example, the subsystems include a foot pedal subsystem 106 including, for example, a foot pedal 108, a fluidics subsystem 110 including an aspiration vacuum 112 and an irrigation pump 114 that connect to tubing 115, an ultrasonic generator subsystem 116 including an ultrasonic oscillation handpiece 118, an intravenous (IV) pole subsystem 120 including a motorized IV pole 122, and a pneumatic vitrectomy cutter subsystem 124 including a vitrectomy handpiece 127, and an imaging and control subsystem 126 including a communication module 130. In this example, a microscope 128 and arm 150 also form a part of the console 102. However, in other embodiments, the microscope 128 and arm 150 are separate from the console 102. To optimize performance of the different subsystems during surgery, their operating parameters differ according to, for example, the particular procedure being performed, the different stages of the procedure, the surgeon's personal preferences, whether the procedure is being performed in the anterior or posterior portion of the patient's eye, and so on. It should be noted that alternative consoles may have alternative subsystems.

The different subsystems in the console 102 comprise control circuits for the operation and control of the respective microsurgical instruments. The computer system 103 governs the interaction and relationship between the different subsystems to properly perform an ocular surgical procedure. To do this, it includes a processor and memory and is preprogrammed with instructions for controlling the subsystems to carry out a surgical procedure, such as an emulsification procedure or a vitrectomy, for example.

In addition, the console 102 includes an input device that permits a user to make selections within a limited scope to control or modify the preprogrammed relationships between different subsystems. In this embodiment, input devices may be incorporated into the console and may include the footpedal 108, a touch screen device responsive to selections made directly on the screen, a standard computer keyboard, a standard pointing device, such as a mouse or trackball, buttons, knobs, or other input devices are also contemplated. Using the input devices, a surgeon, scientist, or other user may select or adjust parameters that affect the relationships between the different subsystems of the console 102. Accordingly, based on a user input, a user may change or adjust the relationships from those that were hard-coded into the console by the system programmers.

In the embodiment shown, still referring to FIG. 1, the console 102 includes an arm 150 that supports the microscope 128. As such, the microscope 128 may be attached to the console 102 and may be positioned at a location proximate the surgical site so that a surgeon may view the surgical site. As will be explained below, when a surgeon wears the wearable user interface 104 and looks through the microscope 128 at the surgical site, he or she may perform the surgery while additional status, state, and parameter information is simultaneously viewable. This may increase the efficiency of the operation because the surgeon need not take his eyes off the surgical site to obtain status information of the system.

The imaging and control subsystem 126 is configured and arranged to present data and information to the wearable user interface 104 for easy and intuitive display to a surgeon during a surgical procedure. The communication module 130 of the imaging and control subsystem 126 may comprise a transceiver used to communicate with the wearable user interface 104. It may communicate settings and/or setting images relating to the surgical site and the console settings. In one embodiment, the transceiver is an RF (Radio Frequency) transceiver enabling wireless communication. It may also communicate via Bluetooth, Wi-Fi (Wireless Fidelity), infrared or other communication method. Wired systems are also contemplated. In addition, the transceiver may receive information and data from the wearable user interface 104. The information and data may include user selections and instructions for operating different aspects of the console 100 and may include information and data relating to the wearable user interface 104 itself, such as battery status and any error information.

FIG. 2 also shows the wearable user interface 104 that can display data relating to system operation and performance during an ocular surgical procedure. The wearable user interface 104 may comprise a display screen 140 and a communication module 142. The wearable user interface 104 may be configured as a monocle or goggles that are worn over the eyes of the surgeon. Other wearable user interfaces may be used, including head-sets, facial shields, or other wearable user interfaces. An advantage associated with a wearable user interface is that the display shows information that may be relevant to the surgery directly to the surgeon without requiring the surgeon to move away from the monocles of the microscope. In addition, the surgeon may move his or her head, and may still view the displayed surgical data.

The display screen 140 on the wearable user interface 104 may be, for example, standard (480i) or high definition (720p, 1080i, or 1080p) display screen that presents images to the wearer. Other screens having other resolutions are also contemplated. In some embodiments, the wearable user interface 104 has particular regions of the screen that are transparent and permit the surgeon to see through, similar to a pair of conventional eyeglasses. As such, the surgeon can look through the microscope 128 to see the surgical environment while still obtaining a benefit of the data display. This may enable the surgeon to look through a microscope, grasp tools see about the surgical room, etc. to maintain an optimal surgical experience.

The communication module 142 receives the transmitted data and information from the communication module 130 of the console 102. It then conveys the information to the display screen 140 for display to the surgeon. In addition, it may convey information and data from the wearable user interface 104 to the communication module 130 on the console 102. In one embodiment, the communication module 142 comprises a transceiver as described above.

Figure 3:
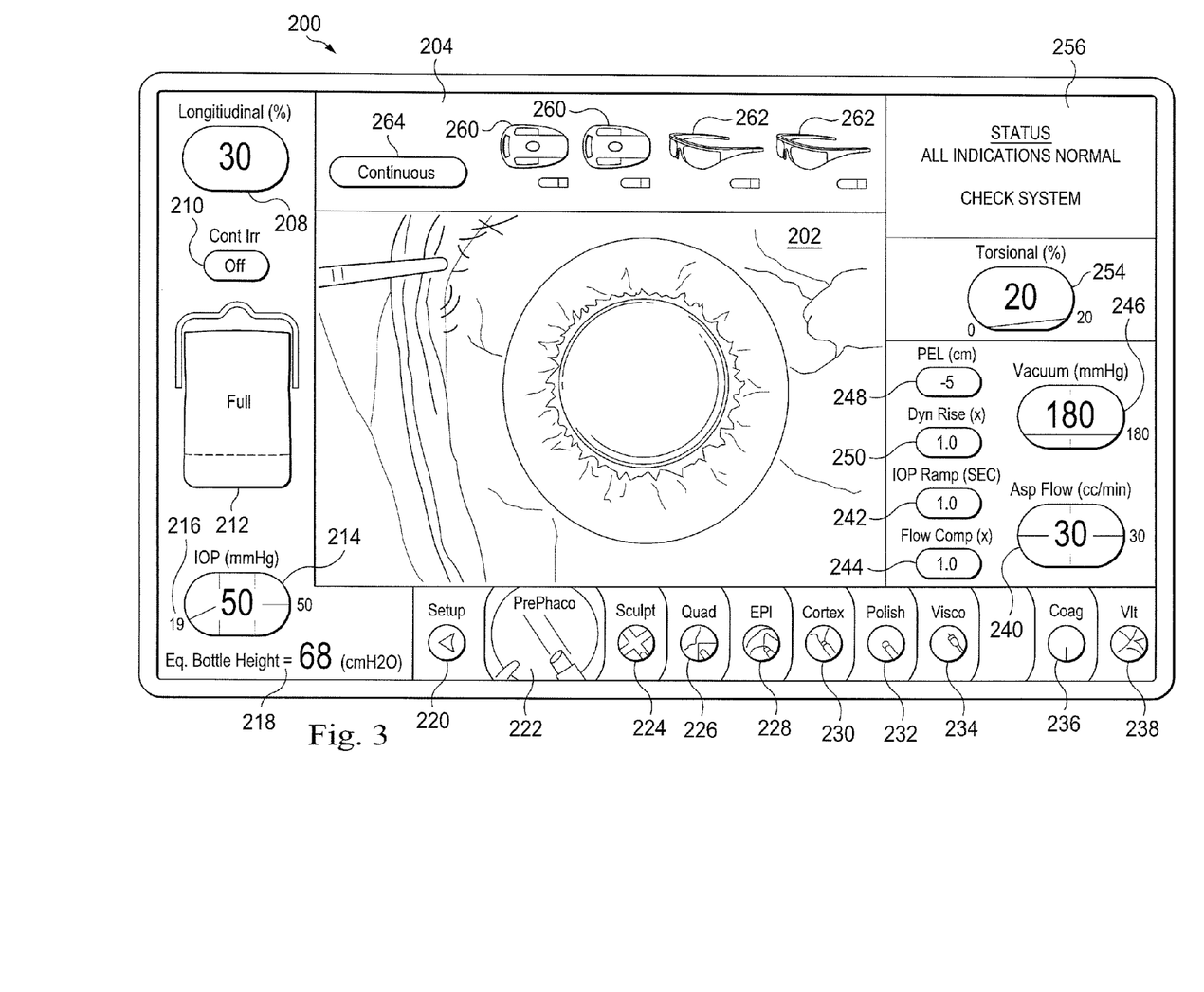
FIG. 3 is an illustration of an exemplary image displayable on a wearable user interface according to an aspect consistent with the principles of the present disclosure.

FIG. 3 shows an exemplary image 200 that may be presented on the display screen 140 during a surgical procedure. It may also be shown on the console display 105. In this embodiment, the image 200 includes a central surgical viewing area 202 configured to display an area of focus and includes a peripheral data display region or display frame 204 about the central surgical viewing area 202 that shows information relating to the surgical process, surgical components, or other parts of the console 102.

Accordingly, in the example shown, the central surgical viewing area 202 is disposed primarily in the central region of the display screen 140 and is sized to permit a surgeon to have a sufficiently large and unobstructed view of the surgical site.

In this embodiment, the central surgical viewing area 202 is a transparent portion of the wearable user interface 104 permitting a surgeon to see through the wearable user interface 104 and into oculars of a microscope to visualize the surgical site in a conventional manner. As such, the surgeon can see and perform the surgery as is done conventionally. However, the display frame 204 provides important surgical status and setting data to the surgeon that can be visualized without turning his head or removing it from the monocles of the microscope. As such, a surgeon does not need to look at the console in order to know which settings are active and the status of the surgical process. Although the display frame 204 is shown as a solid frame with a solid background, some embodiments merely overlay the informational and data elements onto the image viewed by the surgeon. As such, the display frame 204 may have fewer obstructions and the surgeon may feel that he has a larger and more complete view of the surgical site.

In this example, the display frame 204 includes features relating to settings of the console, supply status, and conditions of the patient. For ease of explanation, the exemplary information will be described in detail.

Along the bottom of the display frame 204, the image includes console mode settings that correspond to typical surgical processes. As can be seen, in this exemplary embodiment, the console mode setting includes a selectable Setup icon 220, a PrePhaco icon 222, a Sculpt icon 224, a Quad icon 226, an EPI icon 228, a Cortex icon 230, a Polish icon 232, a Visco icon 234, a Coag icon 236 and a Vit icon 238. These icons show the mode in which the console is operating. Whenever one of these icons is selected, the information and selections displayed are changed as appropriate for the surgical process each of the icons represents. In one embodiment, these settings are changed on the console 102, and the display 200 is updated to show the newest settings. In the embodiment shown, the PrePhaco icon 222 is displayed as being selected.

These icons may be selected by input settings on the console, such as by buttons, knobs, or touch screen on the console or foot pedal. In one embodiment, a knob may be rotated to highlight each selectable icon in turn, and when the desired icon is highlighted an input is made using a button, pressuring the knob, or tapping the foot pedal. Other selection methods are also contemplated.

Along the right side of the exemplary display frame 204 are several data points relating to the fluidics. These include an aspiration flow rate value 240, an IOP ramp value 242, and a flow comp value 244. The aspiration flow rate value 240 indicates the flow rate in cc/min (Cubic Centimeter/minute). In this example, a line across the display indicates whether the flow rate value is on target, above target, and below target. The IOP (Intraocular Pressure) ramp value 242 indicates ramp time in seconds to arrive at the desired flow rate. The flow comp value 244 indicates the setting or rate for compensating for overshoot. Accordingly, overshoot in the aspiration flow is compensated at the set rate of the flow comp value 244.

Also along the right side of the exemplary display frame 204 are a vacuum pressure value 246 in mmHg (Millimeters of Mercury), a PEL (patient eye level) value 248, a Dyn Rise (Dynamic Rise) value 250. The vacuum pressure value 246 represents the vacuum pulled by the pump to achieve the desired aspiration pressure. The PEL value 248 represents the patient eye level to track the basic saline solution or irrigation source input pressure. The Dyn Rise value 250 is used to control the rate of response to overshoot in the vacuum pressure. Again, these may be set on the console 102.

The Torsional setting 254 shows the setting for the direction of ultrasonic vibration delivered by the phacoemulsification handpiece 118. In the example shown, the upper right corner of the image 200 may be an additional viewing window that permits the viewer to see through the wearable headset into the environment. In some embodiments, it may include a live video feed that enables the surgeon to see portions of the environment, such as the surgical site or the instruments tray, for example.

In this example, above the torsional setting 254, the display screen 140 includes a status bar 256. This may be used to present important information to the surgeon during the surgical procedure. In one example, this may include a green light or text indication that all functions and subsystems are operating normally or as expected. Alternatively, the status bar 256 may be arranged to alert the surgeon of unusual conditions that require the surgeon's attention. In some embodiments, the status bar uses color codes and flashing indicators to capture the surgeon's attention as he performs the surgery.

Along the top of the display frame 204, in this example are status indicators identifying the components wirelessly connected to the console 102 and their respective battery levels. In this example, the status indicators include two foot pedals 260 and their battery levels on the frame display and two wearable user interfaces 262 and their battery levels. However, in other embodiments, there is only a single foot pedal and a single wearable user interface.

A state of operation indicator 264 displays to the surgeon whether the console 102 is in a continuous operating mode or whether the console is being run under foot pedal control. In this case, the console is set in continuous mode.

In its upper left corner, the display frame 204 shows a longitudinal parameter 208 that displays to the surgeon the longitudinal setting of the ultrasonic vibration delivered by the phacoemulsification handpiece 118.

The display frame 204 also includes continuous irrigation indicator 210. In the example shown, the continuous irrigation is off. However, it may be switched on at the console 102, and the console will transmit information to generate a different image for viewing on the wearable user interface 104 that shows the continuous irrigation as on.

The display frame 204 also includes an irrigation source level indicator 212. The irrigation source level indicator 212 displays to the surgeon the current level of the irrigation source. The irrigation source is conventionally an IV saline source carried by the IV pole on the console 102. In the example shown, the irrigation source level indicator 212 is shown as full. It also includes a fill line that indicates to the surgeon that the irrigation source is depleted and should be replaced with a full irrigation source. The status is sent from the console 102 to the wearable user interface 104 so that the surgeon can monitor the status of the irrigation source without removing his eyes from the monocles of the microscope. In some embodiments, the irrigation source level indicator 212 may flash, pulse, or change colors, such as to a red color, when the fluid level falls below a preset threshold, thereby more fully drawing the surgeon's attention to the state of the fluid source.

Adjacent the irrigation source level indicator 212, the display frame 204 includes an intraocular pressure (IOP) indicator 214. The IOP indicator displays the value of the IOP for continuous monitoring by the surgeon. Since IOP is a function of both atmospheric pressure and intraocular pressure, some embodiments of the IOP indicator 214 are configured to display secondary values that are used to acquire IOP.

In this example, the IOP indicator 214 displays an atmospheric pressure level 216 at the indicator 214. In this embodiment, the IOP indicator also displays the equivalent bottle height 218. In this example, the equivalent bottle height is set at 68 (centimeters of water (cmH2O)). This is typically determined via a pressure transducer in the irrigation line, and can be adjusted to achieve a desired IOP.

In one embodiment, the above described information is displayed to the surgeon through the wearable user interface as he looks in oculars of a microscope to perform the ocular surgery. Accordingly, the system may operate as though the surgeon is wearing eye-glasses that present the frame around the visual line of sight. If the surgeon were to desire to change the settings or the information, he or she would change them on the console and with the foot pedal, for example. It should be understood that different arrangements of the displayed information are contemplated.

Figure 4:
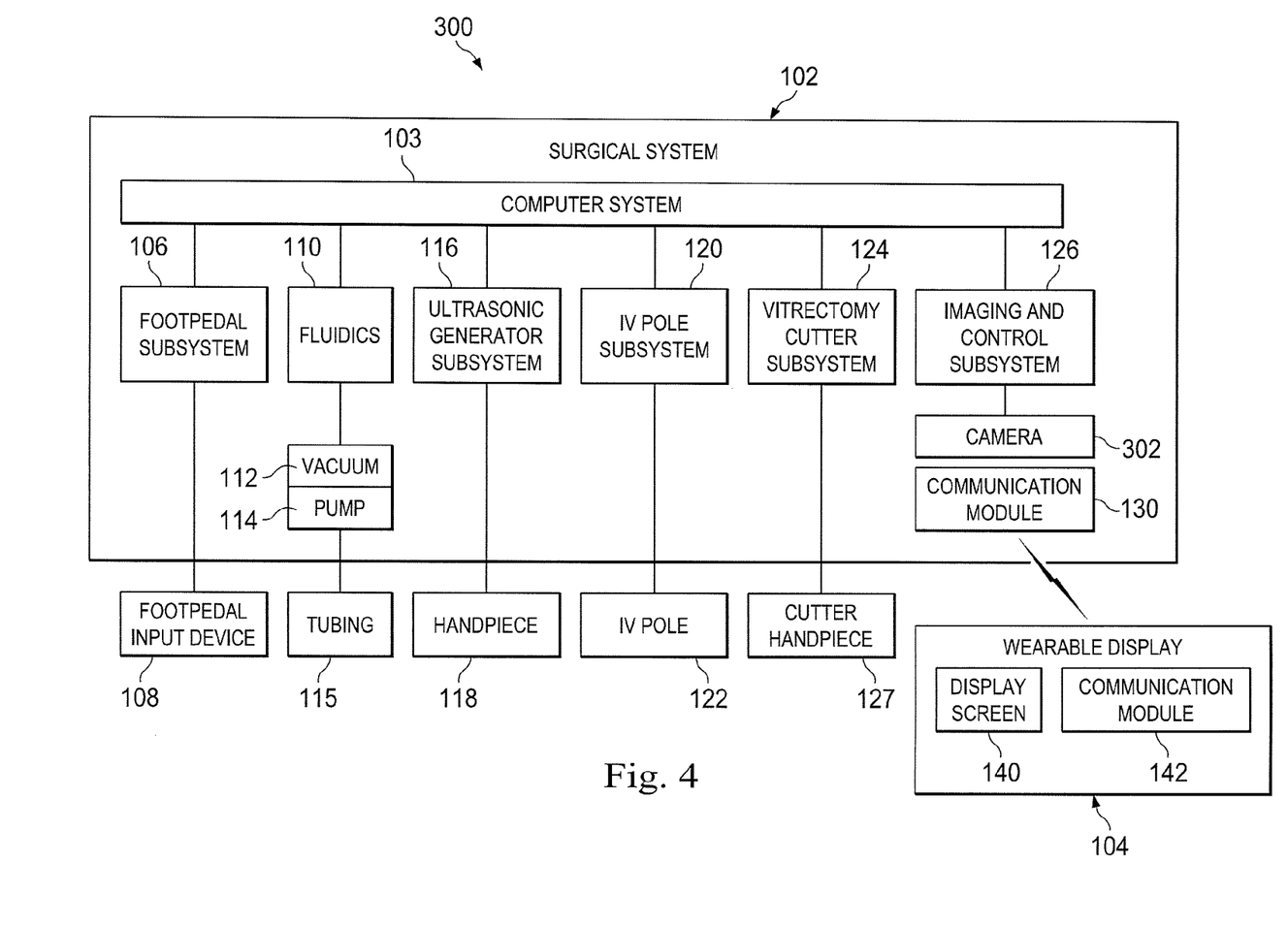
FIG. 4 is an illustration of an exemplary block diagram of another surgical system according to an aspect consistent with the principles of the present disclosure.

FIG. 4 shows another exemplary surgical system 300 that includes a camera 302 as a part of the imaging and control system 126. In one embodiment, the microscope 128 in FIG. 1 may be replaced with the camera 302 or the camera 302 may be disposed alongside the microscope 128 for imaging. As can be seen, the surgical system 300 includes many features similar to that of the embodiments of FIG. 1, and therefore, a description of those is not repeated here.

In this embodiment, the imaging and control subsystem 126 is configured and arranged to capture images with the camera 302 and present image data in addition to status and parameter data to the wearable user interface 104. For instance, referring to FIG. 1, the arm 150 may carry the camera 302 of the imaging and control subsystem 126. By orienting the arm, the camera 302 may be disposed in a location proximate the surgical site so that the camera 302 can capture images of the surgical site. Images from the camera 302 are processed by the imaging and control subsystem 126 and then transmitted by the communication module 130 to the wearable user interface 104.

In one embodiment, the camera 302 is a high definition 3D (three dimensional) imaging camera configured to capture images of the surgical site in a manner enabling the surgeon to view the surgical site and have depth perception at the surgical site that may not be obtained by a traditional camera image displayed on a 2D (two dimensional) display screen. In one embodiment, the camera 302 is associated with oculars disposed adjacent the camera 302 to enable a surgeon to view the surgical site in a traditional manner through a microscope. This may aid the surgeon in aligning the camera 302 at a desired location relative to the surgical site prior to beginning an ocular surgery.

Figure 5:
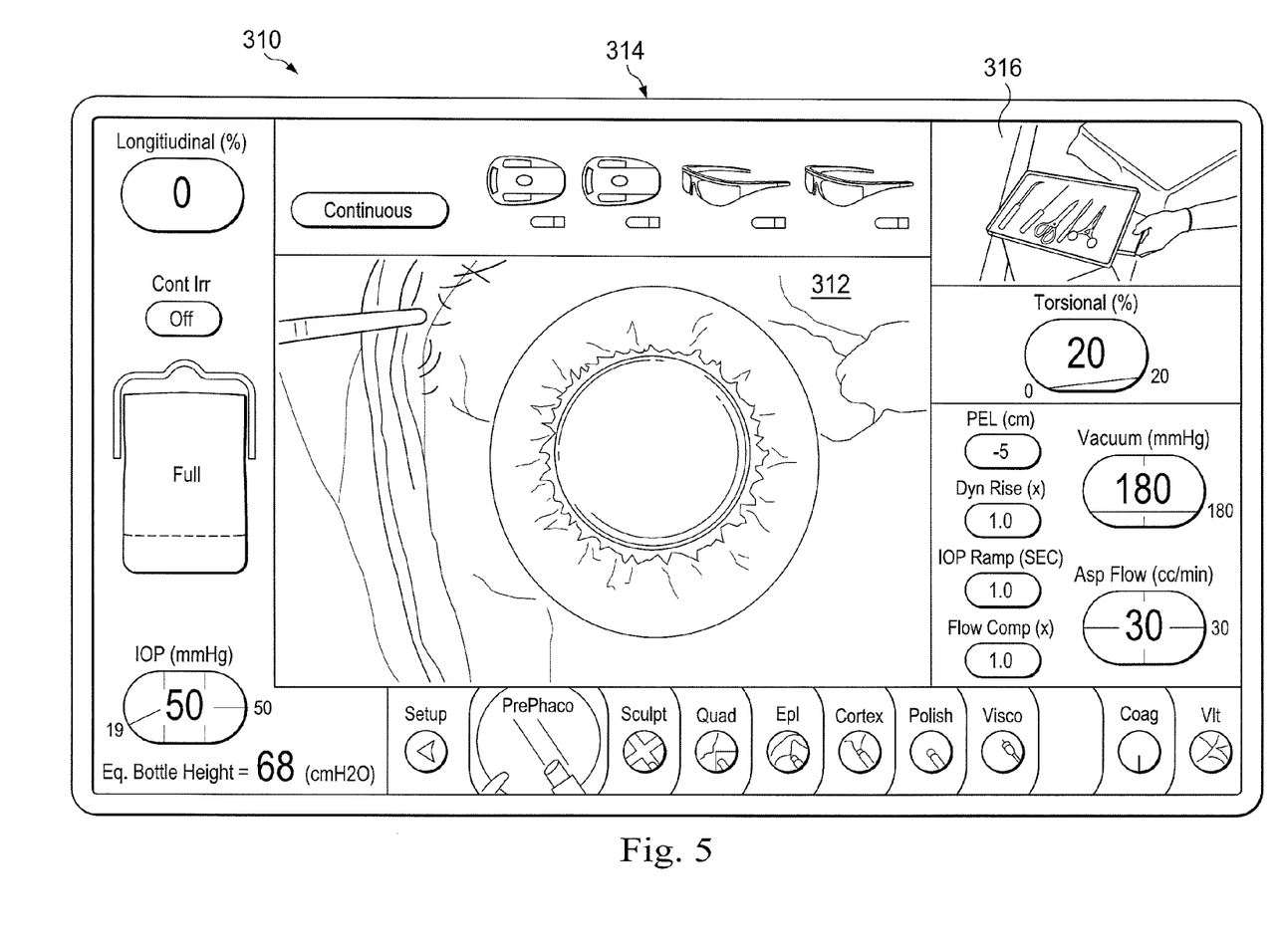
FIG. 5 is an illustration of an exemplary image displayable on a wearable user interface according to an aspect consistent with the principles of the present disclosure.

FIG. 5 shows an example of an image 310 displayed on the display screen of the wearable user interface 104. Similar to the image 200 described in FIG. 3, the image 310 includes a central surgical viewing area 312 and a display frame 314. Since most of the display frame 314 is similar to the display frame 204 in FIG. 3, it will not all be described again in detail. Here, the central surgical viewing area 312 is showing an image captured through the real-time camera 302 that is transmitted to the wearable user interface 104. Accordingly, in this embodiment, the surgeon need not align his head to look through the oculars on the microscope in order to view the surgical site. As such, the surgeon may hold his head more comfortably, and may even move his head during the surgical procedure while still viewing the surgical site and while performing the surgery.

In the embodiment shown, the display frame 314 includes a second display region 316 in place of the status bar shown in FIG. 3. In some embodiments, the second display region 316 is simply a transparent region that the surgeon may look through in order to see the environment. Accordingly, during the surgery, the surgeon may view the environment through the second display region 316 of the wearable user interface 104, while video of the surgical site is displayed in the central surgical viewing area. As such, he or she may be able to view the instrument tray for example and grasp desired instruments or see other parts of the surgical room without removing the wearable user interface 104. In addition, the surgeon can turn and view the console and make any necessary changes or adjustments on the console without removing the wearable user interface 104. He needs only to gaze into the corner that does not have a displayed image.

Figure 6:
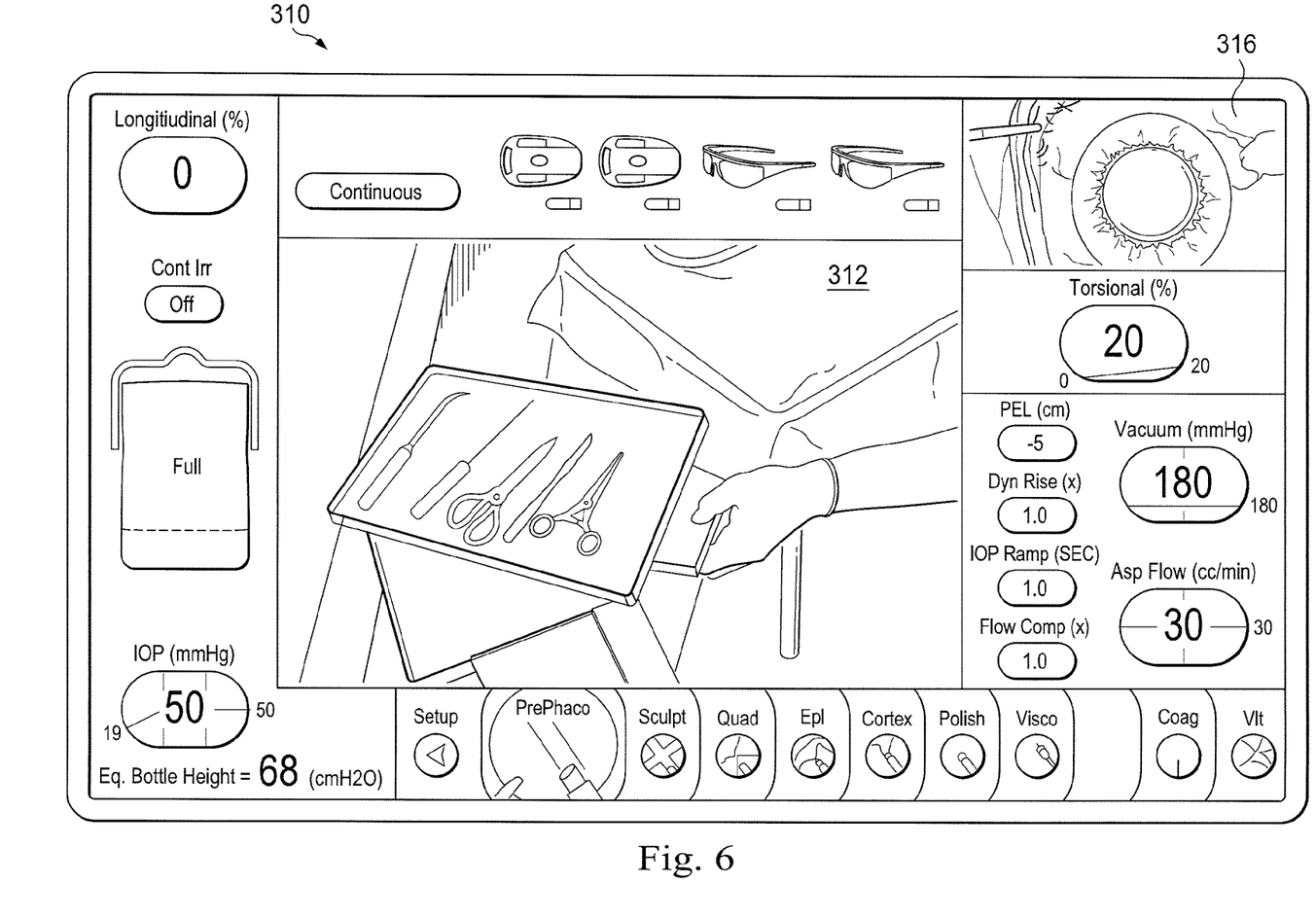
FIG. 6 is an illustration of another exemplary image displayable on a wearable user interface according to an aspect consistent with the principles of the present disclosure.

In one embodiment, the system 100 includes a wearable camera disposed on the wearable user interface 104 itself. This wearable camera may capture and display images in real-time. In this embodiment, since the display in FIG. 5 is showing two captured images, it may replace one for the other as is shown in FIG. 6. That is, if both images are images captured by cameras, either the console 102 or the wearable user interface 104 may permit a surgeon to toggle between the image in the central surgical viewing area 312 and the image in the second display region 316. This is shown in FIG. 6. The user may use any input to toggle between the images, including for example, an input on the wearable user interface or an input on the console 102.

In one embodiment, the display screen 140 comprises a screen for each eye, increasing the depth perception as compared to a conventional image on a 2D screen which may be important to a surgeon during the ocular surgical process.

In the embodiments described above, information and data relating to the surgery and the surgical site is displayed in the display frame. In some embodiments, control of the console 102 is integrated with the images displayed to the surgeon during the surgical procedure. For example, the user may make selections or adjust parameters based on the images in the wearable user interface 104. In one embodiment, the console 100 includes a scroll wheel that moves a cursor about the selectable portions of the display screen. In one example, the icons, values, or regions are highlighted in turn as the user turns the scroll wheel. When the desired icon, value, or region is highlighted, the user may select it using an input, such as a button on the console 102, the wearable user interface 104 or elsewhere. In one embodiment, the selections may be made using the foot pedal 108. For example, if the user were to desire to turn on the continuous irrigation selection 210 in FIG. 2, the user would scroll until the continuous irrigation selector is highlighted, and then select it. This might toggle the continuous irrigation selector 210 from off to on. Likewise, values may be adjusted in a similar manner, including scrolling to increase or decrease the value after it is selected. Accordingly, a surgeon may able to make adjustments to the console operation using the wearable user interface 104.

Figure 7:
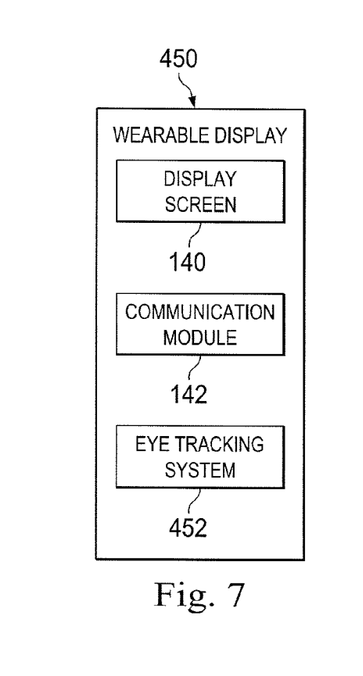
FIG. 7 is an illustration of an exemplary block diagram of another wearable user interface of a surgical system according to an aspect consistent with the principles of the present disclosure.

FIG. 7 discloses an alternative embodiment of a wearable user interface 450 usable in the system 100. In this embodiment, the wearable user interface 450 includes an eye tracking system 452 that permits the console 102 to identify the point of gaze of the surgeon. Based on information obtained from the eye tracking system 452, the system 100 may highlight the particular selectable icon in the surgeon's gaze on the wearable user interface. The surgeon may then select it using an input device, such as, for example, the foot pedal 108. Depending on the selected item, the value may be adjusted further using additional inputs, such as wheels or knobs, keyboards, buttons, etc. As such, the eye tracking system may enable selection and control of the console using the wearable user interface 450.

Figure 8:
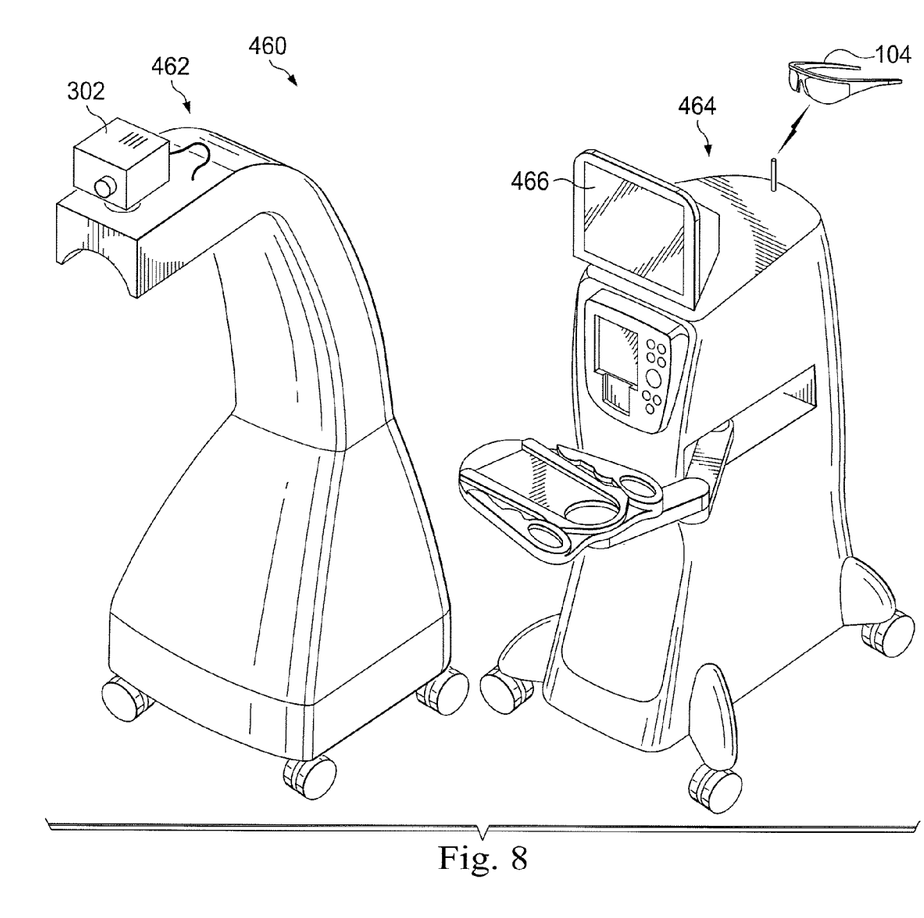
FIG. 8 illustrates another exemplary surgical system according to an embodiment consistent with the principles of the present disclosure.

FIG. 8 shows an alternative system 460 that includes a camera system 462, a console 464, and the wearable user interface 104. The camera system 462 is configured to secure or hold the camera 302 at the desired height. In this embodiment, the camera system 462 is independent of the console 464 and is shaped to be disposed at the head of a surgical bed so that the camera may be located above the eye of a patient on the surgical bed. The console 464 may be in communication with the camera system 462 and may receive live video feed for transmission to the wearable user interface 104.

In this embodiment, the console 464 includes a display screen 466. In one embodiment, the display screen 466 displays the same data and imaging as the wearable user interface 104. Here, the display screen 466 rests on a housing of the console 464 for viewing and access by the operator.

An exemplary method of displaying data to a user includes obtaining information relating the functions, parameters, and settings of a surgical console and parameters relating to the surgery site or the surgery itself. This may include, for example, obtaining information relating to console settings, such as irrigation settings, aspiration settings, and vacuum settings. In addition, this may include obtaining information relating to mode or state settings, such as PrePhaco settings, Sculpting settings, Quad settings, and the other settings identified relative to FIG. 3. This may also include obtaining surgical site parameters relating the patient condition, such as IOP. Finally, this may include obtain information relating to the settings of surgical instruments of the surgical system. For example, this may include obtaining information relating to the longitudinal and torsional ultrasonic vibration profiles. With this information obtained, the information may be organized into a presentable manner as a display frame disposed around a central surgical viewing area of a display.

With the display frame disposed about the central surgical viewing area, the surgeon may use a microscope through the central surgical viewing area, while simultaneously being able to view and monitor the status of the console and other surgical information.

In some aspects, the system obtains a video image of a surgical site from a video camera disposed adjacent the surgical site. The video image may, in some aspects, be organized to fit within the central surgical viewing area of the displayed image. With the image arrangement prepared, the console may transmit the information regarding the image to the wearable user interface for display. In one embodiment, the console sends the data and information relating to the console to the wearable user interface and the camera sends a video feed directly to the wearable user interface. In this embodiment, the wearable user interface organizes and presents the image in the wearable user interface. The surgeon may then perform the surgery while viewing the surgical site on the wearable user interface.

In some embodiments, the surgeon may select and make changes to settings using the wearable user interface. The surgeon may select information or settings displayed on the wearable user interface and may modify or toggle them using input devices. In one embodiment, seeking information or settings for modification may be accomplished using eye tracking technology that tracks the user's gaze. When the system recognizes that the surgeon is gazing at a particular selectable icon or setting, the system may highlight or otherwise identify that icon or setting. It may then be selected by a further input at the console or at the wearable user interface. It may then be adjusted. In one embodiment, the selection may occur by pressing the foot pedal 108.

The systems, devices, and methods disclosed herein may enable a surgeon to more efficiently perform ocular surgical procedures by providing a wearable user interface that presents information and data relating to the surgical parameters and the patient condition so that the surgeon need not remove his gaze from the surgical site to visually see the parameters, possibly resulting in more efficient surgeries. In addition, by having a camera capture the surgical site and displaying it to the surgeon on a wearable user interface, the surgeon may more comfortably perform the surgery.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

I claim:

1. An ocular surgical system comprising:
a surgical console having a fluidics subsystem and an input subsystem;
a first camera configured to communicate first live video of an ocular surgical site, the first camera disposed in a location proximate the ocular surgical site;
a wearable user interface in communication with the console and configured to receive the live video of the surgical site communicated from the camera, the wearable user interface comprising a second camera configured to capture second live video of a view determined by an orientation of the wearable user interface, the wearable user interface further comprising an interface display having:
a centrally disposed surgical viewing area that selectively displays the first live video of the ocular surgical site or the second live video; and
a peripheral data display region configured to display data relating to a surgery or the console, wherein the peripheral data display region displays information received from the surgical console and comprises a second display region to selectively display the second live video or the first live video of the ocular site, the second display region displaying the first live video when the centrally disposed surgical viewing area is displaying the second live video, the second display region displaying the second live video when the centrally disposed surgical viewing area is displaying the first live video.

2. The ocular surgical system of claim 1, wherein the first camera is a 3D camera to capture depth perception on the wearable user interface.

3. The ocular surgical system of claim 2, wherein the interface display comprises a display screen of the wearable user interface that comprises a screen for each eye to display 3D images to a user.

4. The ocular surgical system of claim 1, wherein the first camera is disposed in connection with a microscope, wherein the microscope is disposed on an arm of the surgical console.

5. The ocular surgical system of claim 1, further comprising a foot pedal, wherein the wearable user interface further comprises an eye tracking system configured to highlight a feature of the interface display and wherein the foot pedal is configured to select the highlighted feature upon actuation by a user of the wearable user interface.

6. The ocular surgical system of claim 5, wherein the peripheral data display region displays information relating to ultrasonic vibration parameters.

7. The ocular surgical system of claim 1, further comprising a toggle selector configured to receive input from a user to select either the first live video or the second live video for display in the centrally disposed surgical viewing area, the wearable user interface being configured to simultaneously display the second live video from the second camera and the first live video of the surgical site.

8. The ocular surgical system of claim 1, wherein the peripheral data display region is positioned in a corner of a periphery of the interface display.

9. The ocular surgical system of claim 1, wherein the peripheral data display region displays vacuum pressure and aspiration flow.

10. The ocular surgical system of claim 1, wherein the peripheral data display region displays information relating to ultrasonic vibration parameters.

11. The ocular surgical system of claim 1, wherein the surgical console further comprises a phacoemulsification subsystem.

12. The ocular surgical system of claim 1, wherein the surgical console further comprises a vitrectomy subsystem.

* * * * *